(12) United States Patent
Bergenudd et al.

(10) Patent No.: US 10,555,830 B2
(45) Date of Patent: Feb. 11, 2020

(54) FIXTURE FOR ARM DURING MEDICAL TREATMENT

(71) Applicant: ALL OF IT SCANDINAVIA AB, Bjärred (SE)

(72) Inventors: Hampus Bergenudd, Bjärred (SE); Per Ekdahl, Lund (SE)

(73) Assignee: ALL OF IT SCANDINAVIA AB, Bjärred (SE)

( * ) Notice: Subject to any disclaimer, the term of this patent is extended or adjusted under 35 U.S.C. 154(b) by 245 days.

(21) Appl. No.: 15/300,857

(22) PCT Filed: Mar. 31, 2015

(86) PCT No.: PCT/SE2015/000019
§ 371 (c)(1),
(2) Date: Sep. 30, 2016

(87) PCT Pub. No.: WO2015/152786
PCT Pub. Date: Oct. 8, 2015

(65) Prior Publication Data
US 2017/0020710 A1    Jan. 26, 2017

(30) Foreign Application Priority Data
Apr. 2, 2014   (SE) ...................................... 1430049

(51) Int. Cl.
*A61F 5/37* (2006.01)
*A61M 5/52* (2006.01)
(Continued)

(52) U.S. Cl.
CPC .......... *A61F 5/3761* (2013.01); *A61B 6/0421* (2013.01); *A61B 6/107* (2013.01); *A61G 13/1235* (2013.01); *A61M 5/52* (2013.01)

(58) Field of Classification Search
CPC ........ A61F 5/3761; A61F 5/3776; A61F 5/37; A61G 13/1235; A61G 13/124;
(Continued)

(56) References Cited

U.S. PATENT DOCUMENTS

| 2,119,325 A | * | 5/1938 | Goodhart | ................ | A61M 5/52 |
| | | | | | 248/118 |
| 5,038,434 A | | 8/1991 | Navarrette | | |

(Continued)

FOREIGN PATENT DOCUMENTS

| WO | WO 2006/006836 A1 | 1/2006 |
| WO | WO 2014/123729 A1 | 8/2014 |

*Primary Examiner* — Ophelia A Hawthorne
(74) *Attorney, Agent, or Firm* — Birch, Stewart, Kolasch & Birch, LLP (57) ABSTRACT

A fixture for immobilizing an arm of a patient for insertion of a catheter for coronary investigation and intervention has a fixture board for insertion under a mattress carrying a patient. The fixture board further has a link for attaching an arm holder to the fixture board. The arm holder is arranged adjacent an elbow of the patient and has an arm support and a belt for attaching the arm to the arm support. In addition, a wrist holder is attached to the arm holder for supporting the wrist. The wrist holder may be sterilized and disposable. An instrument table is connected to said fixture board via a link. The distance between the arm holder and the fixture board may be adjustable.

7 Claims, 10 Drawing Sheets

(51) Int. Cl.
*A61G 13/12* (2006.01)
*A61B 6/04* (2006.01)
*A61B 6/10* (2006.01)

(58) Field of Classification Search
CPC ..... A61G 2210/50; A61G 13/12; A61M 5/52; A61B 6/0421; A61B 6/107; A61B 6/04
See application file for complete search history.

(56) References Cited

U.S. PATENT DOCUMENTS

| | | |
|---|---|---|
| 5,845,885 A | 12/1998 | Carnevali |
| 7,055,910 B2 | 6/2006 | Wright |
| 2005/0052066 A1 | 3/2005 | Wright |
| 2008/0203249 A1 | 8/2008 | Priest |
| 2014/0026892 A1* | 1/2014 | Drake ............... A61G 13/124 128/845 |

* cited by examiner

FIXTURE FOR ARM DURING MEDICAL TREATMENT

FIELD OF INVENTION

The present invention relates to a fixture for an arm of a patient. The fixture is especially intended to be used during X-ray investigation and evaluation and during possible balloon expansion of coronary vessels of the heart and similar medical treatments.

BACKGROUND

Heart deceases are the most common cause of death in the Western World.

The most common heart decease is coronary artery obstruction. The coronary arteries provide oxygenated blood to the heart muscle itself. Obstructions result in less blood flow, often resulting in angina pectoris, which is chest pain due to ischemia, i.e. a lack of blood supply, thus a lack of oxygen supply of the heart muscle, generally due to obstruction or spasm of the coronary arteries.

In order to confirm coronary vascular decease, the coronary vessels are exposed to X-ray investigation, which today is considered to be the "Golden Standard". If obstructions or constrictions are found, such constrictions may be treated by balloon expansion or surgery, such as by-pass surgery, or by other methods. Obstructions, such as blood clots, may be dissolved or removed by introduction of suitable agents.

The X-ray investigation and evaluation and other interventions may be performed by inserting a catheter via arteria femoralis or via arteria radialis and advancing the catheter to the area under investigation or for medical intervention.

When the investigation or insertion of a catheter takes place via the radial artery, it may be convenient for the physician to use the right arm of the patient lying in a supine position, since the physician almost always is placed at the right side of the patient.

When the right arm is used and the physician is arranged at the right side of the patient, the arm should be placed along the abdomen in a relaxed position. If the right arm is placed in this position, the palm of the hand is normally faced downward or inward towards the abdomen and the radial artery at the wrist is not easily available. The arm needs to be rotated about 90 degrees around its symmetry axis and the wrist should be turned backward to expose the inner wrist portion, where the radial artery is most easily available. There is a need for a fixture for obtaining and maintaining such a position.

Reference is made to patent publication WO2013/089608A1, which discloses a fixture for immobilization of a left arm of a patient.

A similar problem is encountered during plebotomy procedures as disclosed in U.S. Pat. No. 7,055,910B2. In order to immobilize the arm, there is provided an armrest assembly, which includes an armrest platform with hand and elbow extensions. The assembly is mounted to a swivel base unit that tilts, turns and rotates under the control of a single load control knob to permit placement of a patient's arm in several positions as needed to draw blood. The swivel base unit is mounted on the distal end of a cylindrical riser that can be raised and lowered to a desired elevation by a single load control lever supported by a base securing device that is adapted to be secured to different types of surfaces configurations.

However, the armrest mount of U.S. Pat. No. 7,055,910B2 is made of metal and cannot be used in an environment in which X-ray equipment should be used. The armrest mount is mounted on an armrest, and has to be adjusted to the position of the arm of the patient. If the patient moves, the armrest needs to be readjusted by movement along the armrest and remounting. In addition, there is required some type of support for medical equipment to be used during the treatment.

SUMMARY OF THE INVENTION

Accordingly, an object of the present invention is to mitigate, alleviate or eliminate one or more of the above-identified deficiencies and disadvantages singly or in any combination.

In an aspect, there is provided a fixture for being attached to an arm of a patient, comprising: an arm holder arranged adjacent an elbow of the patient and comprising an arm support and a belt for attaching the arm to the arm support and a wrist holder attached to the arm holder for supporting the wrist, characterized by a link for attaching the arm holder to a fixture board intended to be arranged on a bed board for a patient. The fixture board may comprise a plate intended to be inserted between said bed board and a mattress, onto which said patient is arranged. The plate may comprise a chamfered edge for making said insertion more easy.

In an embodiment, the distance between the arm holder and the fixture board is adjustable. The link may comprise a first swivel joint arranged at said fixture board, a second swivel joint arranged at said arm holder and a link arm for connecting said first and second swivel joints. The length of the link arm may be adjustable.

In a further embodiment, the fixture may comprise an instrument table, which is connected to said fixture board via a link.

The fixture may be used in a percutanous coronary intervention procedure.

BRIEF DESCRIPTION OF THE DRAWINGS

Further objects, features and advantages of the invention will become apparent from the following detailed description of embodiments of the invention with reference to the drawings, in which.

DETAILED DESCRIPTION OF EMBODIMENTS

Below, several embodiments of the invention will be described. These embodiments are described in illustrating purpose in order to enable a skilled person to carry out the invention and to disclose the best mode. However, such embodiments do not limit the scope of the invention. Moreover, certain combinations of features are shown and discussed. However, other combinations of the different features are possible within the scope of the invention.

When a catheter should be inserted during X-ray investigation and possible balloon expansion of coronary vasculature of the heart, the most common way to insert such a catheter has up to now been insertion into the femoral artery, since the femoral artery is sufficiently large and extends directly and straight to the aortic arc and subsequently to the coronary arteries. However, since the femoral artery is large, there is also a concomitant risk of blood leakage complications.

As an alternative, the use of the radial artery in the arm has been suggested. The physician is normally placed at the right side of the patient and has a heavy lead apron in order to shield the physician from X-rays. Thus, it may be convenient for the physician to use the right arm of the patient.

The embodiments shown below are intended to be used at the right arm of the patient. However, the fixture may alternatively or additionally be used at the left arm of the patient.

Figure 1:
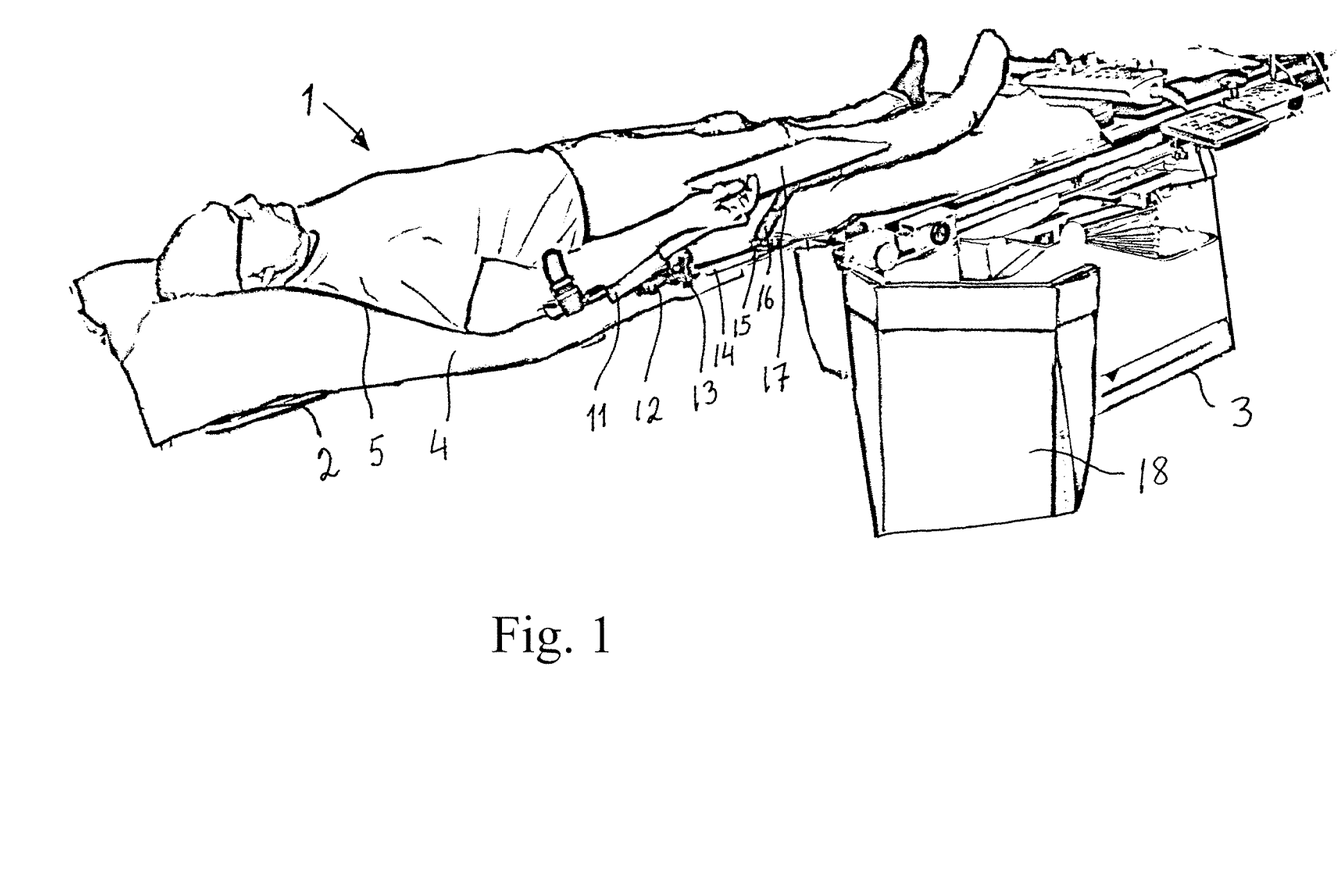
FIG. 1 is a perspective view of a bed on which a patient is arranged having his right arm immobilized by a fixture according to a first embodiment of the invention.

FIG. 1 shows a patient 1 lying on a bed board 2 in a supine position. The bed board 2 is supported by a large stand 3, which may be fixed in position, for example screwed to the floor. The bed board 2 is made of a thin board of a X-ray-transparent material. The bed board 2 is suspended by the stand 3 so that the bed board extends freely out from the stand in a cantilever fashion. Thus, the bed board 2 with a patient 1 can be exposed to X-rays so that the insertion of a catheter can be monitored in real time.

A heavy lead protection shield 18 is attached to the stand 3 and may be folded to a position below the bed board in order to protect the lower portion of the physician from X-ray radiation.

The part of the bed board which supports the head and the upper portion of the body of the patient must be free from any metal parts. Thus, the bed board is made of carbon fibers and plastics material, so that a sufficiently stiff bed board is obtained.

The bed board has no edges which can support an arm fixture of the type used in the prior art U.S. Pat. No. 7,055,910B2. Thus, a new type of fixture is required.

FIG. 1 shows a first embodiment of an arm fixture. The fixture comprises an arm holder 11, which is attached to a first swivel joint 13 by a first link 12. The first swivel joint 13 is attached to a board 14. Moreover, the fixture comprises an instrument table 17, which is attached to a second swivel joint 15 via a second link 16. The second swivel joint 15 is also attached to the board 14. The board 14 is inserted between the bed board 2 and a mattress 4 arranged on the bed board 2. In addition, a protecting sheet 5 may be arranged on the mattress.

Figure 2:
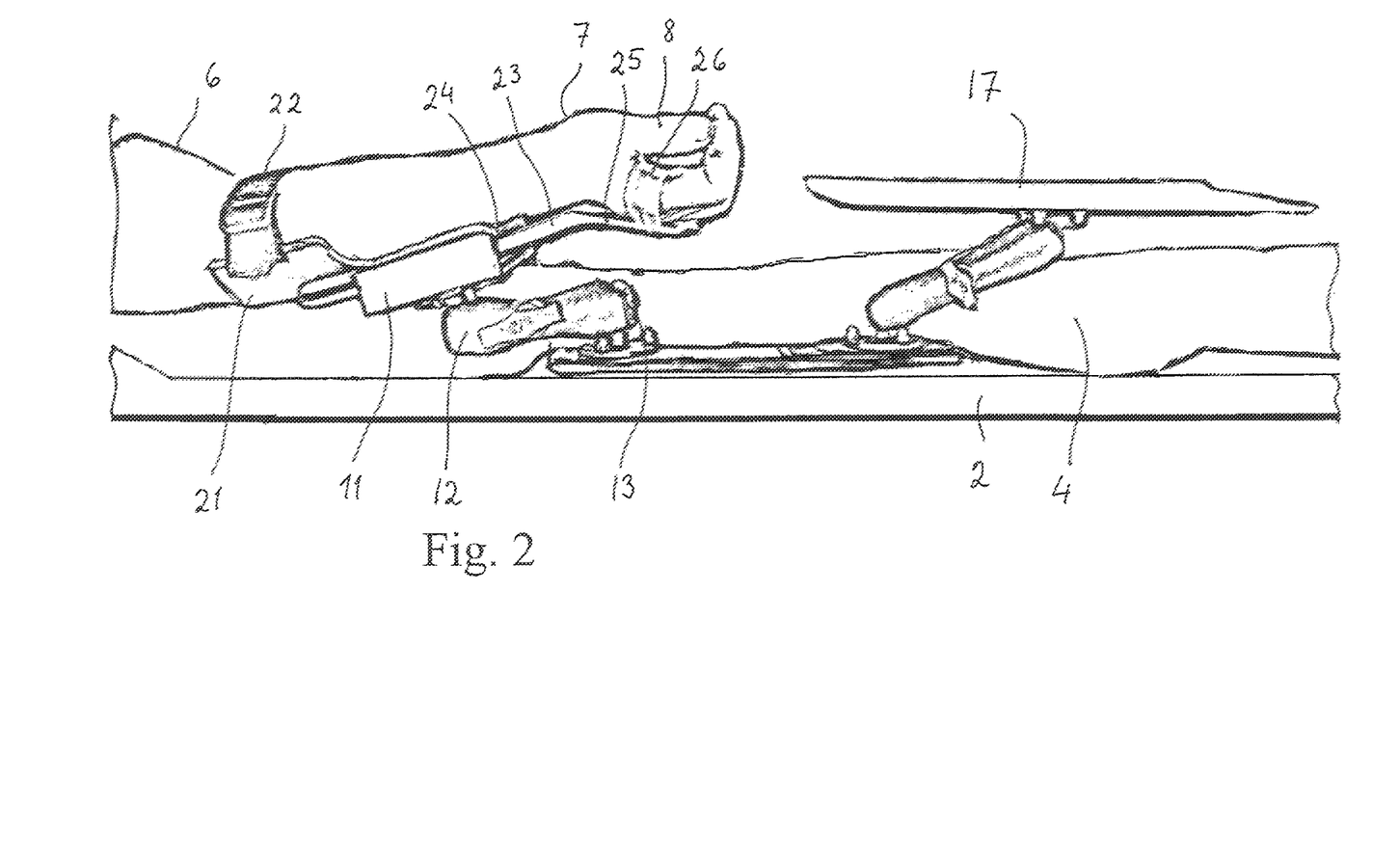
FIG. 2 is a perspective view of a portion of FIG. 1 in an enlarged scale.
Figure 3:
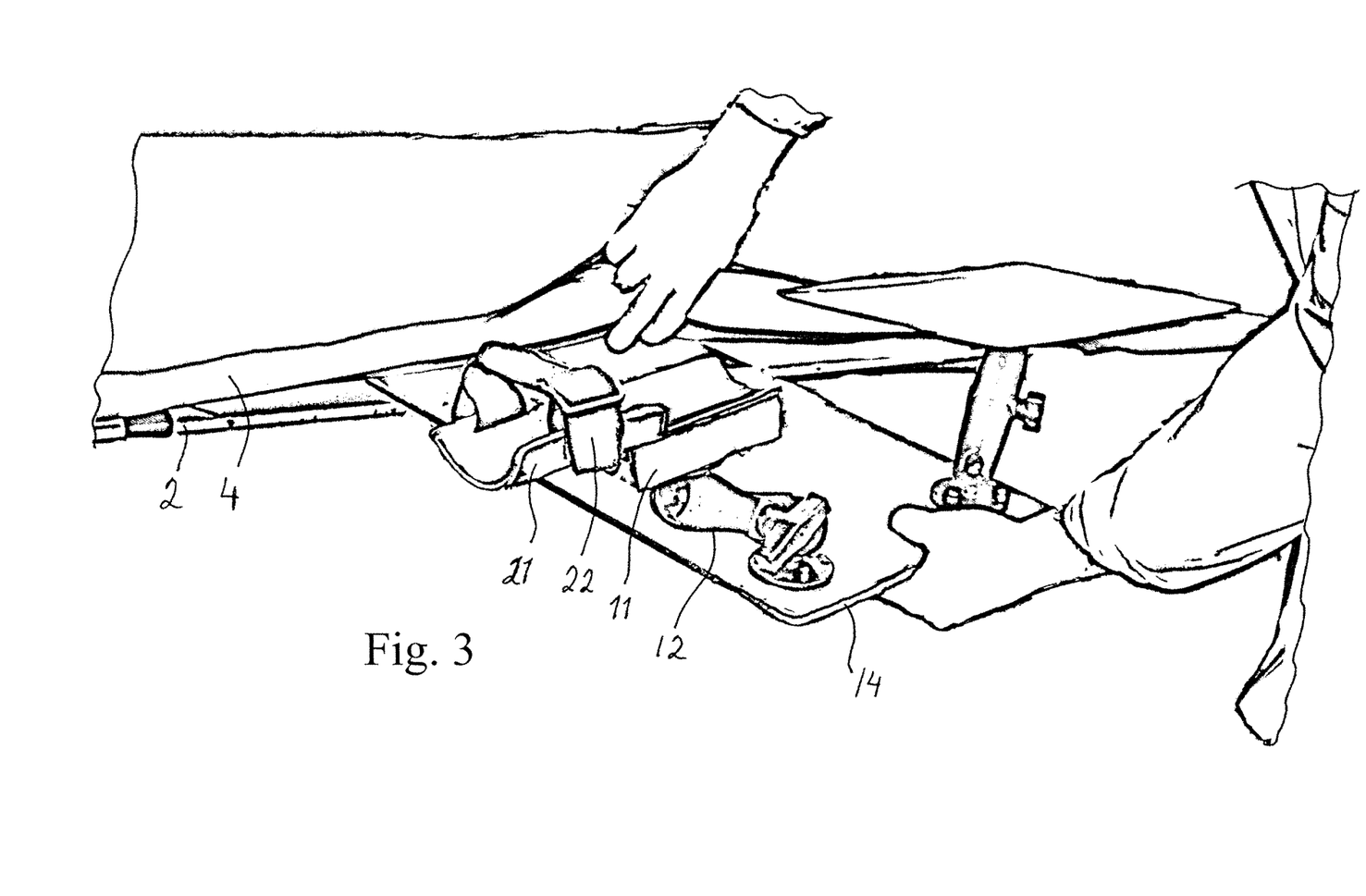
FIG. 3 is a perspective view of the fixture during insertion between the bed and a mattress arranged on the bed.

The arm fixture according to the first embodiment is shown in more detail in FIGS. 2 and 3. The arm holder 11 comprises an arm support portion 21 provided with an adjustable belt 22, arranged to encircle an arm 6 adjacent an elbow of the arm in order to immobilize the arm on the arm support portion 21. In addition, a wrist support portion 23 is insertable in a slit 24 of the arm holder 11. The wrist support portion 23 comprises an angled outer portion 25 provided with a belt or tape 26. The angle is arranged at the outer side of the wrist 7 of the arm and the tape 26 is arranged around the hand above the thumb 8 as shown for immobilizing the hand to the wrist support portion 23. Thus, the wrist will be arranged in an angled position with an open angle, whereby the arteries at the inner side of the wrist will be exposed to the physician.

The wrist support portion 23 is the only part, which needs to be sterilized. The wrist support portion 23 may be provided as a disposable product, which is used only one time and then discarded. The other parts of the embodiment can be cleaned in an aseptic way as is practice in a hospital.

As shown in FIG. 3, the bed board 2 is provided with a mattress 4. The bed board 2 and the mattress are normally provided with friction material so that the mattress will retain its position on top of the bed board 2. Such friction material makes it normally practically impossible to insert the fixture board 14 between the bed board and the mattress, especially if a patient is lying on the mattress—unless the mattress is lifted as shown in FIG. 3.

The fixture board 14 may be made of a non-friction material, which will enable the fixture board 14 to be inserted between the bed board and the mattress.

In another embodiment, the mattress is provided with an area lacking said friction material. The area without friction material is arranged in the position, wherein the fixture board 14 is to be inserted.

In a further embodiment, there is arranged a sheet between the mattress and the bed board in the position, wherein the fixture board 14 is to be inserted. The sheet may be a double sheet, like a pillowcase. The fixture board 14 is inserted inside the pillowcase.

In these embodiments, the fixture board 14 is insertable between the bed board and the mattress even in the situation when a patient is lying on the mattress. In addition, the fixture board is, at least partly, moveable in the longitudinal direction in order to adapt the board and the arm holder 11 in a predetermined position.

The fixture according to the embodiment is used in the following manner, see FIG. 2. When a patient is in need of an arm fixture, the fixture board 14 is inserted between the bed board 2 and the mattress 4 as indicated in FIGS. 2 and 3. Then, link 12 and the arm holder 11 are arranged in a position, in which the arm support portion 21 is positioned adjacent an elbow of a patient. The link 12 is tightened so that the position of the arm holder 11 becomes fixed and the belt 22 is tightened around the arm. The link 12 may be further adjusted during this procedure. The fixture board 14 may be moved in the direction along the bed in order to be in a correct position for supporting the arm when the arm is attached to the fixture.

Then, the wrist holder 23 is inserted in the slit 24, or may have been arranged in the slit from the start. The wrist holder is adjusted to a predetermined position with the angle opposite the wrist and the tape 26 is arranged around the hand. Now the position according to FIG. 2 has been obtained. Finally, the instrument table 17 is arranged in a predetermined position, preferably in a horizontal position and is covered by a sterile cloth. The patient is now ready for treatment.

There is no metal parts in the arm fixture of the embodiment, but all details are made from plastics material, which are transparent to X-ray radiation. Thus, the insertion and advancement of a catheter through the arm artery can be monitored.

Figure 4:
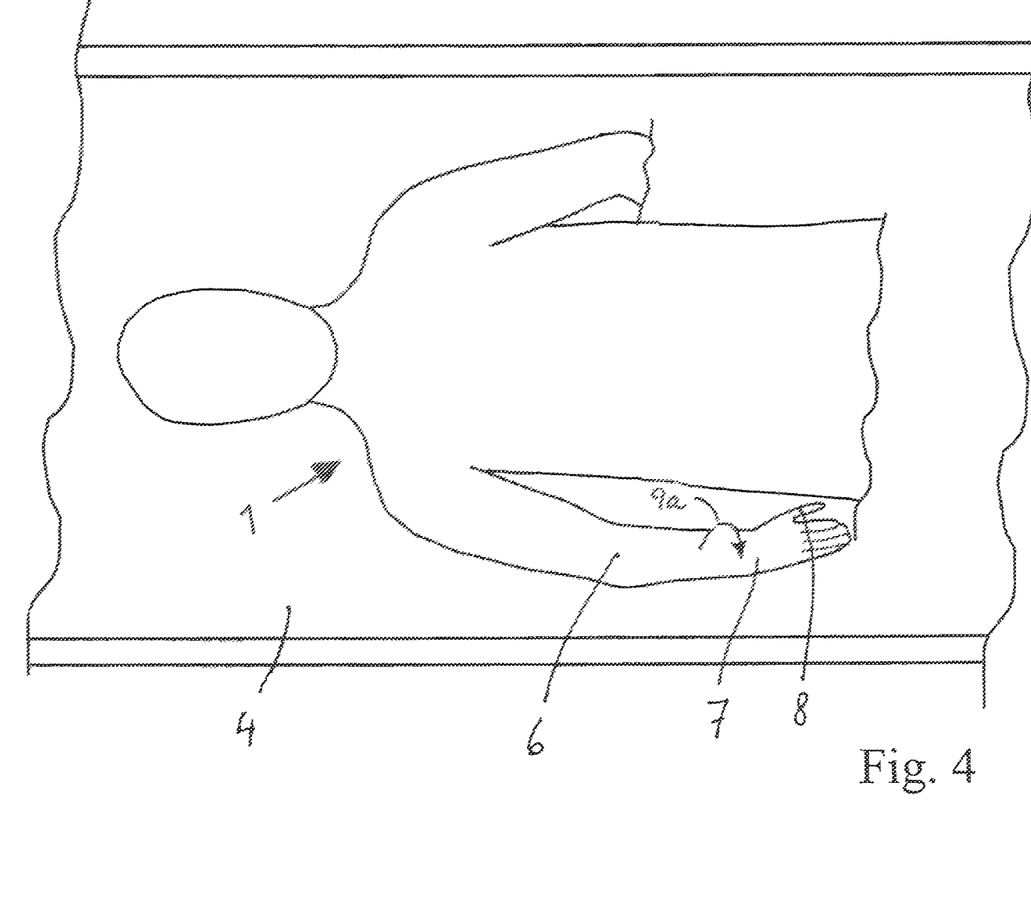
FIG. 4 is a schematic plan view of a patient positioned on a bed.

FIG. 4 shows the patient 1 lying on the bed board mattress 4 in a relaxed supine position with the right arm 6 resting at the side of the abdomen with the hand approximately at the waist.

The palm of the hand is facing downward or inward towards the abdomen, as appears from FIG. 4 and the thumb 8 is directed towards the patient. Thus, the palm of the hand and the inner side of the wrist 7 is facing inwardly, toward the abdomen and the radial artery at the inner side of the wrist is not conveniently available.

The expressions "inner" and "outer" are intended to mean positions at the normal arm position. Thus, the inner side of the arm is the side of the arm normally facing the abdomen, for example in the position shown in FIG. 4. The outer side of the arm is the portion of the arm facing away from the abdomen. The inner side of the hand, i.e. the palm, is facing downward or toward the abdomen in the position shown in FIG. 4.

As shown by arrow 9a in FIG. 4, the hand and the wrist 7 should be rotated about 90° around the symmetry axis of the arm in order to expose the radial artery at the inner side of the wrist. In this position, the palm of the hand faces upward and is substantially parallel with the abdomen and the thumb 8 faces outward, i.e. the palm of the hand is oriented in a substantially horizontal direction when the patient is arranged in the supine position shown in FIG. 5. In this position of the arm and the wrist as shown in FIG. 5, the radial artery of the right arm is conveniently available for insertion of a catheter in the artery.

Figure 5:
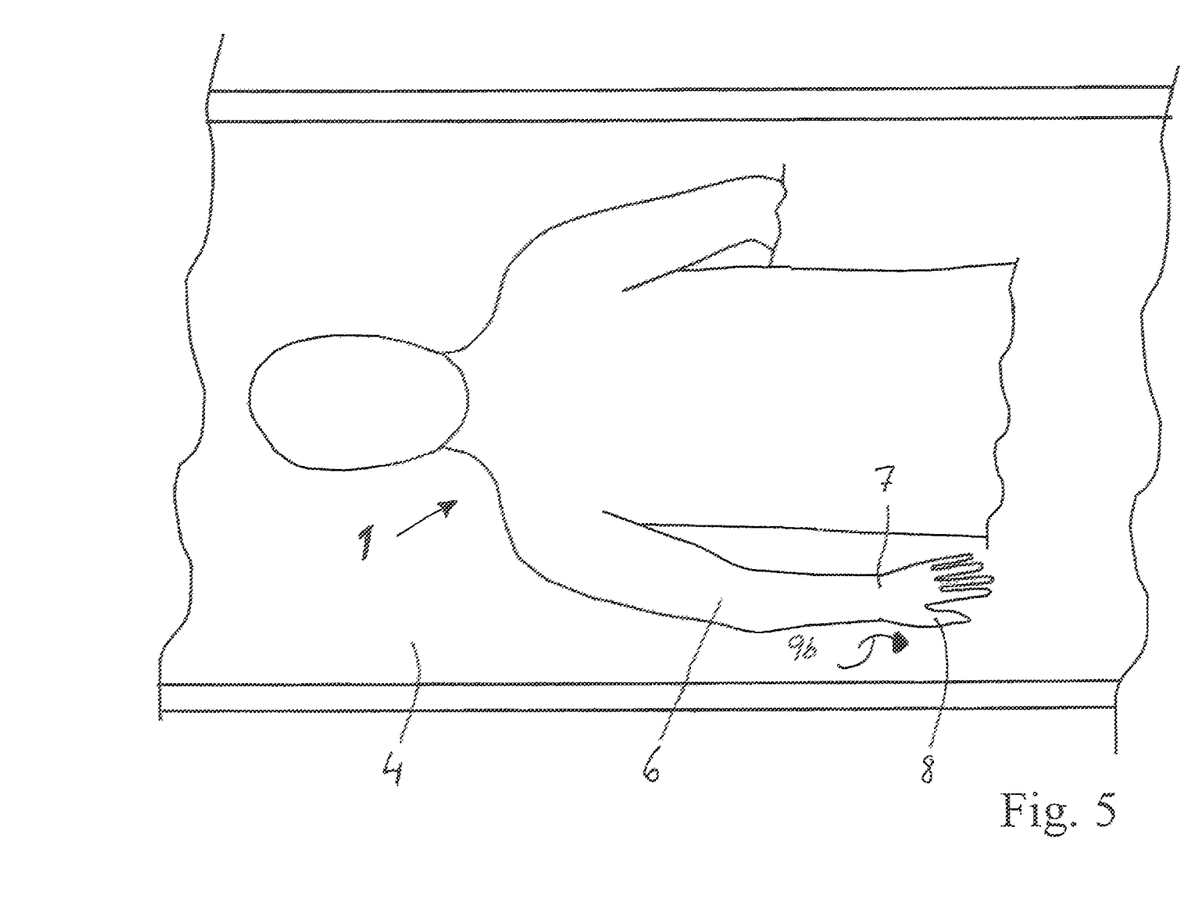
FIG. 5 is a schematic plan view similar to FIG. 4 with the arm in a correct position.

In addition, the wrist should be turned so as to open the angle of the wrist, as shown by arrow 9b in FIG. 5. The expression "opening" the angle of the wrist is intended to mean that the angle between the forearm and the palm of the hand becomes larger than 180 degrees. In this way the radial artery will be conveniently available.

As an alternative to the radial artery, the physician may use an ulnar artery, which is also conveniently available in the position shown in FIG. 5.

During use, the table 17 may be covered by a sterile surgical cloth, for example of cotton. Then, the required instruments, such as peangs, forceps etc and medical devices, such as canulas and hoses, etc are arranged at the table in order to be conveniently positioned to the surgican.

Figure 6:
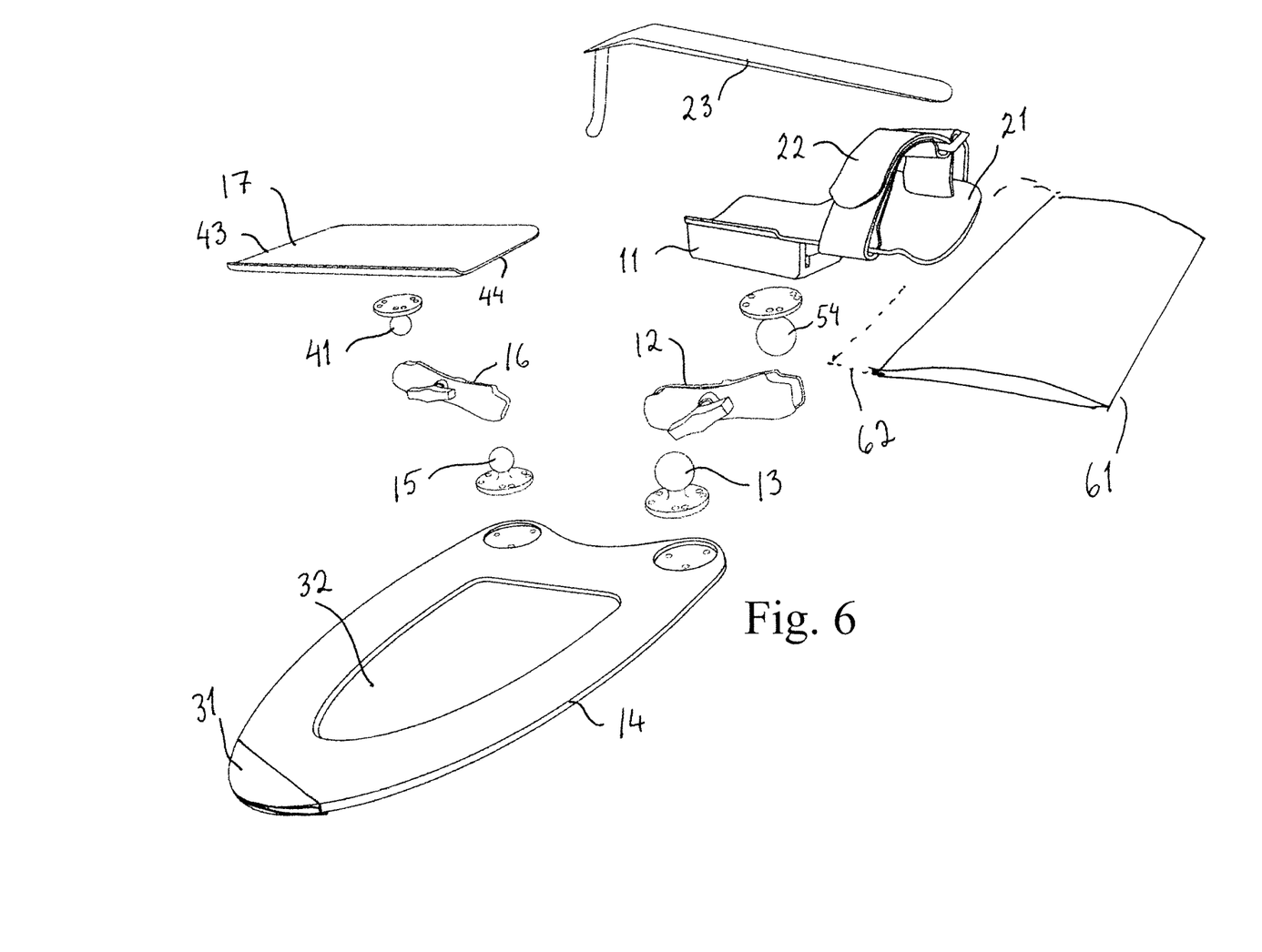
FIG. 6 is an exploded perspective view of a fixture according to a second embodiment of the invention.

FIG. 6 shows the parts of the embodiment of FIGS. 1 to 3 in more detail. The fixture board 14 is substantially oval and rounded and may have a depth (perpendicular to the bed) of about 40 cm and a length (parallel to the bed) of about 20 cm. The inner side may be chamfered as shown by reference numeral 31 in order to make it more easy to insert the fixture board. The fixture board may be provided with one or several holes 32 in order to make the board less heavy.

The swivel joints 13 and 15 may be attached to the fixture board 14 by an adhesive. Alternatively, small screws of metal may be used, since such screws will not be interfering with any X-ray picture that the physician might want to see. Alternatively, screws made of plastic material may be used.

The links 12 and 16 may be of a conventional design, for example as shown in the patent document U.S. Pat. No. 5,845,885A and shown in FIG. 10. Any type of link that is able to immobilize the instrument table 17 and the arm holder 11 in a desired position can be used.

The instrument table 17 is provided with a swivel joint 41 attached to the bottom side of the instrument table 17, by adhesive or by screws. The instrument table 17 is provided with a rim 42, which is arranged for preventing blood from dripping from the instrument table. Similar rims may be arranged at the side edges 43 and 44.

As further shown in FIG. 6, the side facing the physician is provided with a shallow recess, so that the physician is able to stand closer to the bed without contacting the board. In this manner, possible unintended interference of the board by the physician is avoided.

The board 14 is provided with a relatively broad edge so that the board is easily gripped and arranged between the bed board and the mattress.

Figure 7:
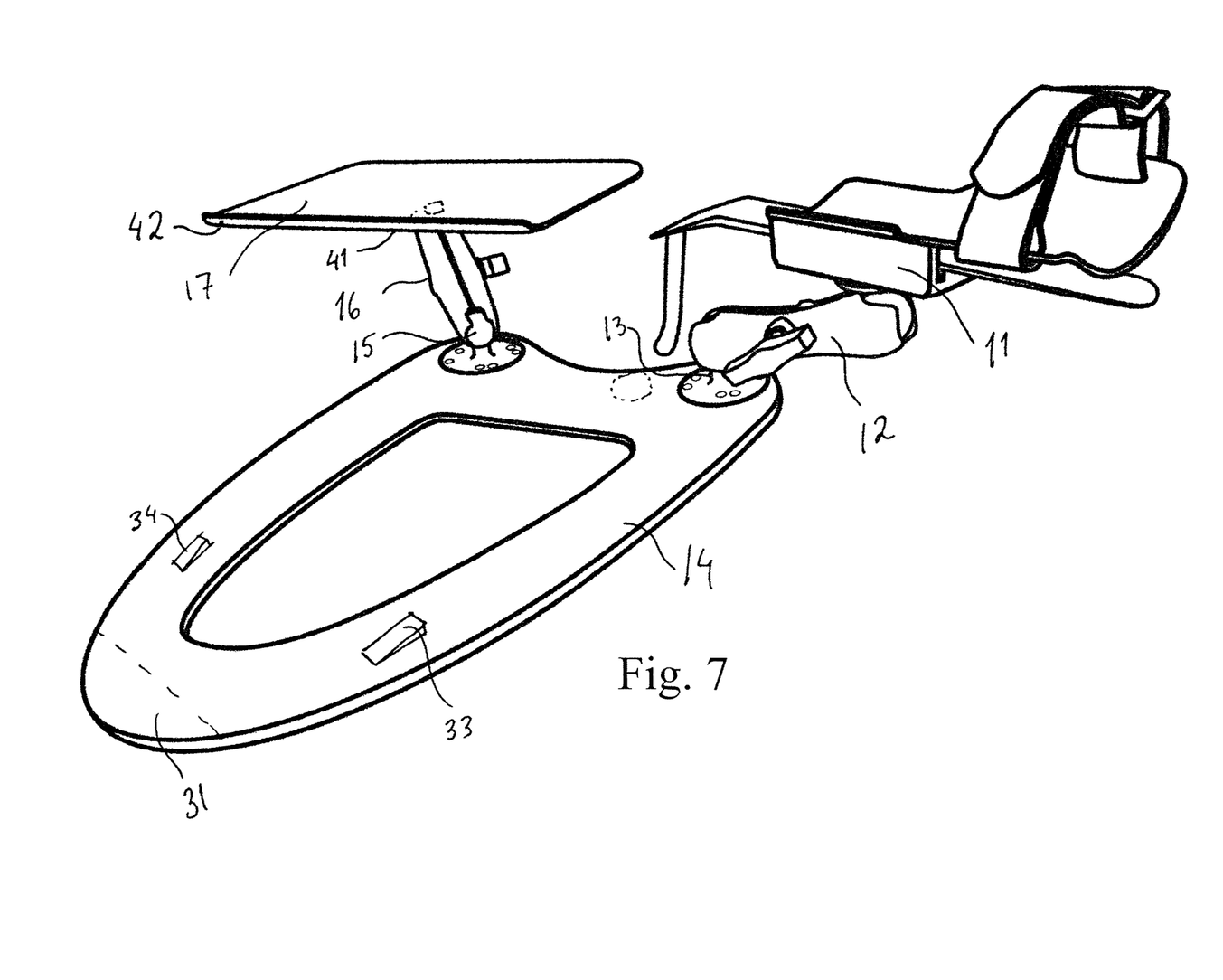
FIG. 7 is a perspective view of the fixture according to FIG. 6 in a mounted position.

FIG. 7 shows the device according to the first embodiment in a mounted position. Thus, the instrument table 17 has been connected to the board 14 by arranging the link arm 16 connecting the swivel joint 15 of board 14 with the swivel joint 41 of the instrument table. In the same manner, the link arm 12 interconnects swivel joint 13 of the board 14 with the swivel joint 54 of the arm holder 11.

One or several triangular protrusions 33, 34 may be arranged at the board 14 as shown in FIG. 7. The protrusions 33, 34 do not prevent easy insertion of the board 14 beneath the bed board 2 and the mattress 4, but prevents unintentional withdrawal of the board 14. In addition, the protrusions 33, 34 prevent dislocation of the board 14 in the lateral direction parallel to the bed length direction.

Figure 8:
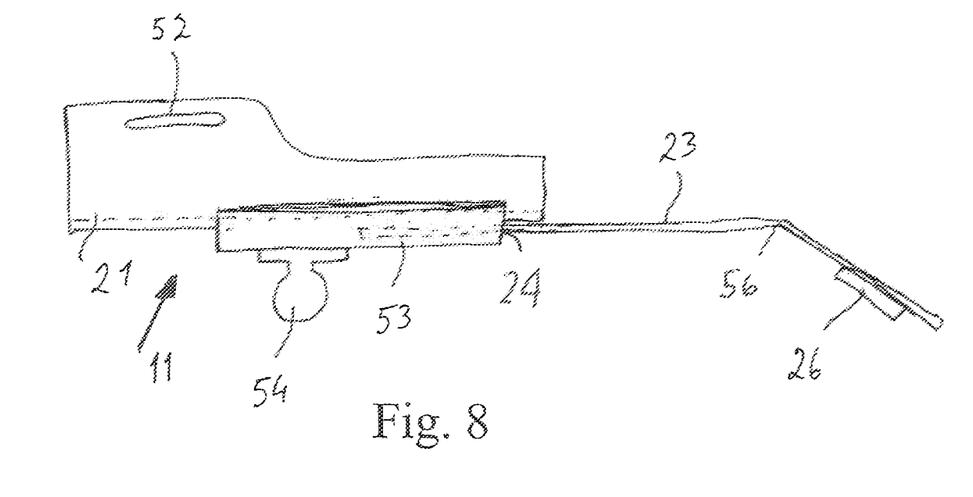
FIG. 8 is a detail view of the arm fixture portion of a second embodiment.

The arm holder 11 is shown in more detail in FIG. 8. The arm holder 11 comprises a support portion 21 provided with slits 52 for a belt. The support portion 21 is arranged in a holding portion 53 provided with a swivel joint 54 for connection to said link 12. The holding portion 53 comprises the slit 24 for insertion of the wrist support portion 23. The wrist support portion has an angle 56, which is intended to be arranged at the outer side of the wrist. The angle may be about 30 degrees. The tape 26 is arranged at the outer part of the wrist support portion.

The wrist support portion may be free to move in the slit 24. Alternatively, a locking screw (not shown) is arranged in the slit 24 for locking the wrist support portion in a predetermined position.

The swivel joint 54 may be arranged more to the left as shown in FIG. 8 in order to better support the weight of the arm. In another embodiment, the swivel joint is arranged in the middle of the holding portion 53.

It may be desired to move the arm holder 11 back and forth along the arm in order to adjust the arm holder in relation to the position of the arm of the patient. This can be performed by moving the entire fixture board 14 back and forth. However, such movements can be difficult to perform and can also be undesirable of other reasons.

Figure 9:
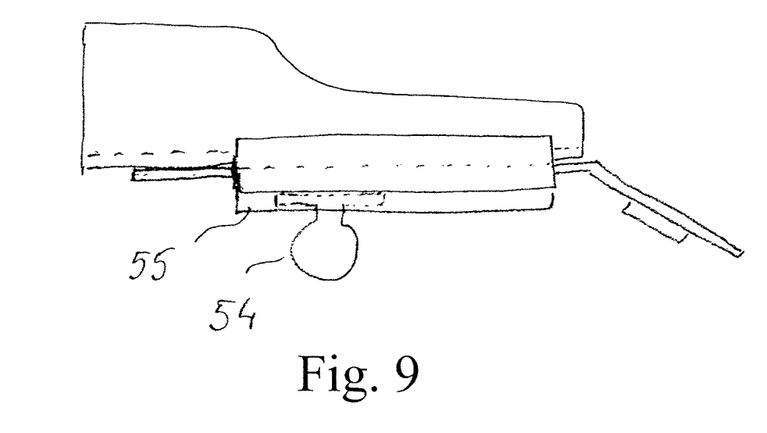
FIG. 9 is another detail view of the arm fixture portion of a third embodiment.

In a further embodiment, the swivel joint 54 is arranged in a longitudinal groove 55 arranged at the bottom side of the holding portion 53 as shown in FIG. 9. Additionally or alternatively, the swivel joint 13 in the fixture board 14 may be adjustable in the length direction toward or away from the other swivel joint 15 and lockable in a predetermined position. Additionally or alternatively, the link 12 may have an adjustable length, for example being telescopic.

The fixture board 14 may be insertable in a pillowcase, as shown in FIG. 6. The pillowcase 61 may have a width which is slightly larger than the length of the fixture board 14. Alternatively, the width of the pillowcase 61 may be larger as indicated by broken lines 62 in order to allow some movement of the fixture board 14 in the length direction. The pillowcase 61 is arranged between the bed board and the mattress before the patient is placed on the mattress. The pillowcase 61 may be made from a woven or non-woven material, such as cloth or may be made from thin boards of a rigid material, such as tree or plastics material.

Figure 10:
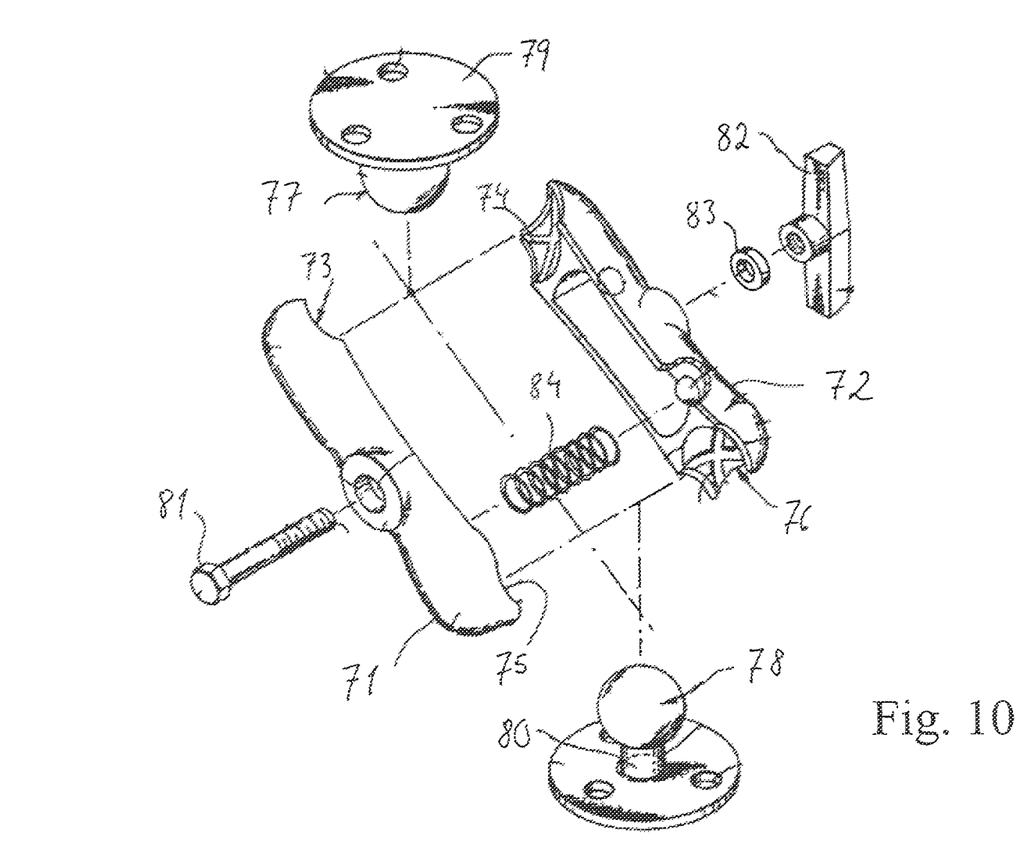
FIG. 10 is an exploded view in perspective of a fixture link used in the embodiment of FIGS. 1 to 3.

FIG. 10 shows a link arm, which may be used in the embodiments as described above. The link arm comprises a left house portion 71 and a right house portion 72. The upper and lower ends of each house portion is provided with partly spherical recesses 73, 74, 75, 76, having the same radius as two spherical swivel joint balls 77 and 78. The swivel joint balls are attached to support plates 79 and 80, which are arranged to be attached (for example by screws) to a device or member to be supported and interconnected by the link arm. The two house portions 71 and 72 are connected to each other by a screw 81 and a nut 82 and a washer 83. A spring 84 keeps the two housing portions at a distance from each other. The recesses 73, 74, 75 and 76 are arranged partly around the balls 77 and 78 when the screw 81 and the nut 82 interconnects the house portions 71 and 72. When the nut 82 is tightened, the recesses are pressed against the balls and the link arm is locked in the adjusted position. The balls 77 and 78 are provided with friction material. In addition, the recesses may be provided with friction material. The link arm may be manufactured by a plastics material, or partly or entirely in a metallic material.

The embodiments disclosed above are intended to be used during Cardiovascular X-ray investigations and interventions in a Cath-Lab department of a hospital. As indicated by several researchers, the transradial, rather than the transfemoral, approach to precutanous coronary intervention has become of great interest, see for example the article by Rao, Sunil V. "The Transradial Approach to Percutaneous Coronary Intervention." Journal of the American College of Cardiology 55.20 (May 18, 2010): 2187-95.

There are other medical methods during which it may be desired to immobilize the right arm in the position shown, for example in emergency situations when fast and convenient access to the arm artery is desired. Such a situation may be during ambulance transports.

Another medical method in which the fixture may be used may be the introduction of cold saline in the arm artery for cooling of the body as soon as possible after a brain injury, such as brain hemorrhage or stroke or a heart infarct. About 500 to 1000 ml cold saline is introduced in the body as soon as possible to induce hypothermia.

A further medical method in which the fixture may be used is the localization and dissolution of clots or obstructions in other positions than the heart.

In the embodiments, links comprising two swivel joints and a link arm are used. However, other types of links may be used, such as parallel connected link arms.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims or embodiments, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Although the present invention has been described above with reference to specific embodiment and experiments, it is not intended to be limited to the specific form set forth herein. Rather, the invention is limited only by the accompanying claims and, other embodiments than those specified above are equally possible within the scope of these appended claims.

The invention claimed is:

1. A fixture configured to be attached to an arm of a patient, comprising:
    an arm holder configured to be arranged adjacent an elbow of the patient and comprising an arm support and a belt configured to attach the arm to the arm support;
    a wrist holder attached to the arm holder configured to support the wrist; and
    a link for attaching the arm holder to a fixture board configured to be arranged on a bed board for a patient, wherein a distance between the arm holder and the fixture board is adjustable, said link including,
        a first swivel joint arranged at said fixture board,
        a second swivel joint arranged at said arm holder, and
        a link arm connecting said first and second swivel joints.

2. The fixture according to claim 1, wherein a length of the link arm is adjustable.

3. The fixture according to claim 1, wherein a distance between the arm holder and the second swivel joint is adjustable.

4. The fixture according to claim 1, wherein the fixture board comprises a plate intended to be inserted between said bed board and a mattress, configured for supporting said patient.

5. The fixture according to claim 1, wherein said plate comprises a chamfered edge.

6. The fixture according to claim 1, further comprising an instrument table, which is connected to said fixture board via a link.

7. The fixture according to claim 3, further comprising an instrument table, which is connected to said fixture board via a link.

* * * * *